(12) United States Patent
Rowe

(10) Patent No.: US 10,568,657 B2
(45) Date of Patent: Feb. 25, 2020

(54) CANNULATION SITE SELECTION APPARATUSES AND METHODS

(71) Applicant: Fresenius Medical Care Holdings, Inc., Waltham, MA (US)

(72) Inventor: Gary Joseph Rowe, San Diego, CA (US)

(73) Assignee: Fresenius Medical Care Holdings, Inc., Waltham, MA (US)

( * ) Notice: Subject to any disclaimer, the term of this patent is extended or adjusted under 35 U.S.C. 154(b) by 394 days.

(21) Appl. No.: 15/396,791

(22) Filed: Jan. 2, 2017

(65) Prior Publication Data
US 2018/0185059 A1 Jul. 5, 2018

(51) Int. Cl.
| | |
|---|---|
| *A61M 5/00* | (2006.01) |
| *A61B 17/34* | (2006.01) |
| *A61M 1/36* | (2006.01) |
| *A61B 5/00* | (2006.01) |
| *A61M 1/30* | (2006.01) |
| *A61B 90/00* | (2016.01) |

(52) U.S. Cl.
CPC .......... *A61B 17/3403* (2013.01); *A61B 5/489* (2013.01); *A61M 1/30* (2013.01); *A61M 1/3661* (2014.02); *A61B 2017/3411* (2013.01); *A61B 2090/061* (2016.02); *A61B 2090/3937* (2016.02)

(58) Field of Classification Search
CPC ........ A61B 17/3403; A61B 2017/3411; A61B 2090/061; A61B 2090/3937; A61B 34/25; A61B 90/06; A61B 90/39; A61B 2090/067
See application file for complete search history.

(56) References Cited

U.S. PATENT DOCUMENTS

| | | | | |
|---|---|---|---|---|
| 4,228,796 A | * | 10/1980 | Gardiner | A61M 5/427 604/116 |
| 4,930,525 A | * | 6/1990 | Palestrant | A61B 17/3403 128/898 |
| 6,024,723 A | | 2/2000 | Cota | |
| 2004/0153031 A1 | * | 8/2004 | Van Kaauwen | A61M 5/427 604/116 |
| 2005/0267396 A1 | * | 12/2005 | Dame | A61M 1/3653 604/4.01 |

(Continued)

FOREIGN PATENT DOCUMENTS

| | | |
|---|---|---|
| EP | 2145642 | 1/2010 |
| WO | WO 00/10642 | 3/2000 |

(Continued)

OTHER PUBLICATIONS

Brouwer et al., "Optimizing Hemodialysis Cannulation Methods: Techniques and strategies to preserve vascular access," Endovascular Today, Feb. 2009, 58-63, 6 pages.

(Continued)

*Primary Examiner* — Rebecca E Eisenberg
(74) *Attorney, Agent, or Firm* — Fish & Richardson P.C.

(57) ABSTRACT

In one aspect, a cannulation site selection apparatus includes a flexible member, a first marking on the flexible member, and an array of cannulation site selection markings on the flexible member, wherein the array of cannulation site selection markings is positioned at a set distance from the first marking, and wherein the cannulation site selection markings are spaced at set distances from one another.

17 Claims, 12 Drawing Sheets

(56) References Cited

U.S. PATENT DOCUMENTS

| | | |
|---|---|---|
| 2007/0237307 A1 | 10/2007 | Suddaby |
| 2010/0015590 A1* | 1/2010 | Kiss ..................... A61M 5/427 434/267 |
| 2011/0007951 A1 | 1/2011 | Mil'shtein et al. |
| 2015/0216613 A1 | 8/2015 | Schilling |
| 2017/0340840 A1* | 11/2017 | Sweis ................... A61B 90/39 |

FOREIGN PATENT DOCUMENTS

| | | |
|---|---|---|
| WO | 20090136982 | 11/2009 |
| WO | 2014209552 | 12/2014 |
| WO | 2015085019 | 6/2015 |

OTHER PUBLICATIONS

International Search Report in International Application No. PCT/US2017/068793, dated May 24, 2018, 20 pages.
International Preliminary Report on Patentability in Application No. PCT/US2017/068793, dated Jul. 2, 2019, 12.

* cited by examiner

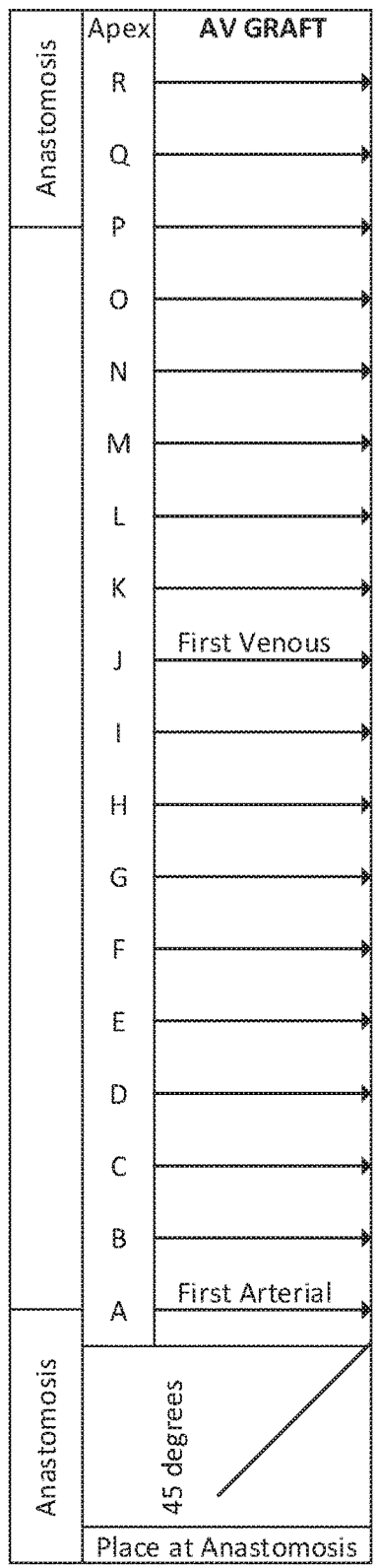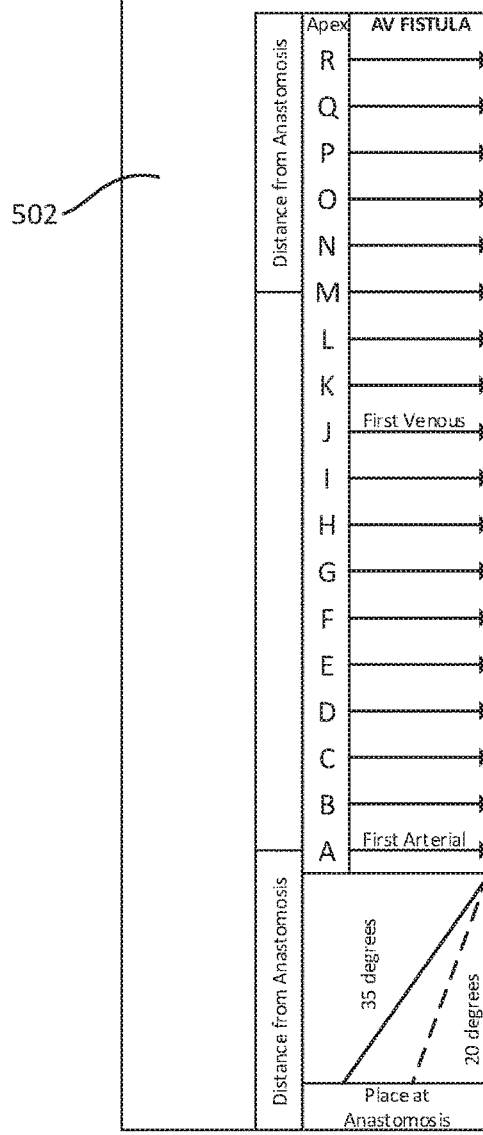
FIG. 5A
FIG. 5B

CANNULATION SITE SELECTION APPARATUSES AND METHODS

TECHNICAL FIELD

This disclosure relates to cannulation site selection apparatuses and methods.

BACKGROUND

During hemodialysis ("HD"), the patient's blood is removed from the patient and then passed through a dialyzer of a dialysis machine while also passing a dialysis solution or dialysate through the dialyzer. A semi-permeable membrane in the dialyzer separates the blood from the dialysate within the dialyzer and allows diffusion and osmosis exchanges to take place between the dialysate and the blood stream. These exchanges across the membrane result in the removal of waste products, including solutes like urea and creatinine, from the blood. These exchanges also regulate the levels of other substances, such as sodium and water, in the blood. The cleansed blood is then returned to the patient. In this way, the dialysis machine acts as an artificial kidney for cleansing the blood.

Various other procedures similarly involve removing blood from the patient for treatment or processing and then returning the blood to the patient.

SUMMARY

In one aspect, a cannulation site selection apparatus includes a flexible member, a first marking on the flexible member, and an array of cannulation site selection markings on the flexible member, wherein the array of cannulation site selection markings is positioned at a set distance from the first marking, and wherein the cannulation site selection markings are spaced at set distances from one another.

In some implementations, the cannulation site selection markings are spaced at set distances appropriate for use with an arteriovenous fistula.

In some implementations, the cannulation site selection markings are spaced at set distances appropriate for use with an arteriovenous graft.

In some implementations, the array of cannulation site selection markings includes a quantity of cannulation site selection markings such that a user can cannulate the patient at a site corresponding to a different cannulation site selection marking for three weeks of treatment.

In some implementations, the array of cannulation site selection markings includes a quantity of cannulation site selection markings such that a user can cannulate the patient at a site corresponding to a different cannulation site selection marking for six weeks of treatment.

In some implementations, the cannulation site selection apparatus also includes an angle guide marking arranged to represent an angle at which the user can insert a needle into a patient. In some cases, the angle guide marking is configured to guide a user in cannulating an arteriovenous fistula. In some cases, the angle guide marking is configured to guide a user in cannulating an arteriovenous graft.

In some implementations, the array of cannulation site selection markings includes cannulation site selection markings for cannulating the apex and sides of a vessel wall.

In some implementations, the flexible member includes cannulation site selection markings on first and second sides of the flexible member.

In some implementations, the cannulation site selection apparatus further includes cannulation site selection labels indicating a first available arterial cannulation site and a first available venous cannulation site.

In some implementations, the flexible member is translucent.

In some implementations, the flexible member defines notches along an edge of the flexible member and the notches are spaced at set distances from one another and correspond with the cannulation site selection markings.

In some implementations, the flexible member defines holes spaced at set distances from one another and the holes correspond with the cannulation site selection markings.

In some implementations, the cannulation site selection apparatus further includes a key on the flexible member, the key describing the array of cannulation site selection markings. In some cases, the key includes a cannulation site rotation plan.

In some implementations, the first marking and the cannulation site selection markings are substantially permanent so as to withstand repeated sterilization.

In another aspect, a method of selecting cannulation sites includes placing a first marking of a cannulation site selection apparatus at a first location on a patient such that a first cannulation site selection marking is adjacent to a prior cannulation site of a vessel and cannulating the vessel at a site corresponding to a second cannulation site selection marking, wherein the second cannulation site selection marking is spaced at a set distance from the first cannulation site selection marking.

In some implementations, the method further includes cannulating the vessel at a site corresponding to a third cannulation site selection marking, wherein the third cannulation site selection marking is spaced at a set distance from the second cannulation site selection marking. In some cases, the site corresponding to the second cannulation site selection marking is cannulated to provide arterial access to the vessel and the site corresponding to the third cannulation site selection marking is cannulated to provide venous access to the vessel.

In some implementations, the first available cannulation site is cannulated to provide access to the vessel for single-needle hemodialysis.

In another aspect, a method of selecting cannulation sites for hemodialysis includes placing a first marking of a cannulation site selection apparatus at a first location on a patient, determining a number of cannulation site selection markings located at viable locations for cannulation along a vessel, calculating a number of treatments that can be completed before repeating a cannulation site based on the determined number of cannulation site selection markings located at viable locations for cannulation along a vessel, and creating a site selection rotation plan for the number of treatments calculated.

In another aspect, a method of buttonhole cannulation for hemodialysis includes placing an angle guide marking of a cannulation site measuring apparatus at a cannulation site and cannulating the vessel with a needle at an angle following the angle guide marking.

In some implementations, the needle is inserted to create a scar tissue channel for buttonhole cannulation.

In some implementations, the needle is inserted along an existing scar tissue channel.

Implementations can include one or more of the following advantages.

In certain implementations, the cannulation site selection apparatus has markings which can be used to create and implement a cannulation site rotation plan. As a result, the cannulated vessel is allowed increased healing time before re-cannulation occurs at a particular site. Further, properly spacing and rotating cannulation sites, as achieved using the cannulation site selection apparatus, can extend the life of the patient's vascular access (e.g. an arteriovenous fistula or arteriovenous graft) and reduce the likelihood of failure of the vascular access.

In certain implementations, the cannulation site selection apparatus has cannulation site selection markings which can be used to cannulate a vessel over a number of treatments in a standardized and repeatable pattern. A user may create a cannulation site rotation plan after comparing these markings to a patient's vessel. Additionally, in certain implementations, the cannulation site selection apparatus has an angle guide marking, so the user has a reference for cannulating the vessel at a proper angle for the type of vessel being accessed for treatment. As a result, in following the markings of the cannulation site selection apparatus, vessel cannulation, and site selection can be standardized across users.

In certain implementations, the cannulation site selection apparatus is made of a flexible material. In some implementations, the material from which the cannulation site selection apparatus is formed is sufficiently flexible such that the apparatus can be bent around a patient's body part (e.g., arm, leg, neck, etc.) without breaking. As a result, the apparatus may be easily contoured along a patient's vessel, allowing a cannulation site selection plan to be created and implemented for patients regardless of their vessel's geometry.

Other aspects, features, and advantages will be apparent from the description and drawings, and from the claims.

BRIEF DESCRIPTION OF THE DRAWINGS

FIGS. 5A and 5B are views of first and second sides, respectively, of yet another cannulation site selection apparatus with markings on the first side to be used with an arteriovenous graft and with markings on the second side to be used with an arteriovenous fistula.

DETAILED DESCRIPTION

Figure 1:
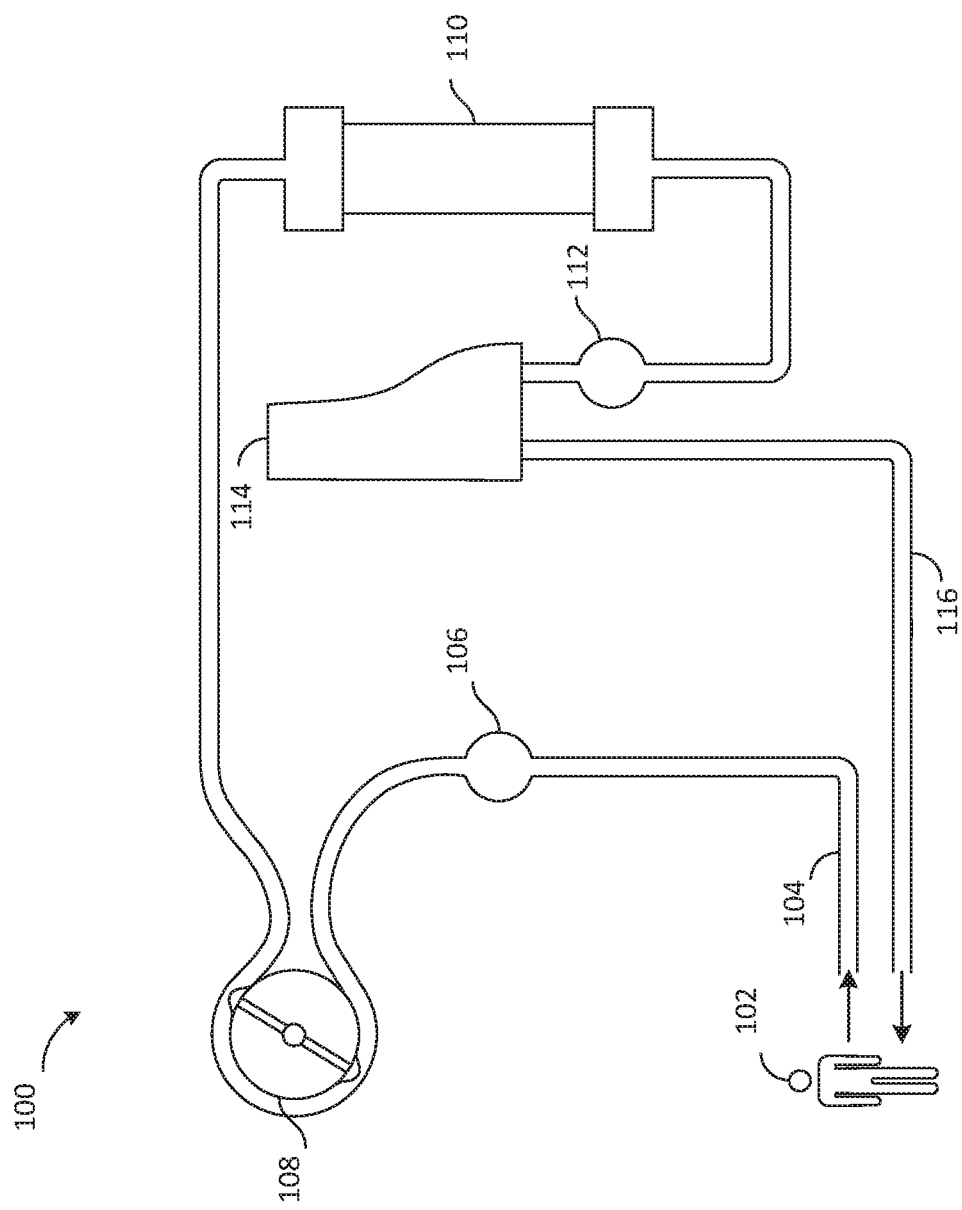
FIG. 1 is a schematic of an extracorporeal blood circuit of a hemodialysis machine.

Referring to FIG. 1, a hemodialysis system includes an extracorporeal blood circuit 100. The extracorporeal blood circuit 100 is connected to a patient 102 along a vascular access, which may be an arteriovenous (AV) fistula or an arteriovenous (AV) graft. For many hemodialysis treatments, two vascular access points are required—an arterial access point and a venous access point. These points are typically created before each treatment by inserting needles connected to arterial and venous lines 104, 116 of the blood line set into an arterial needle site and a venous needle site, respectively. After connection to the patient, the blood flows through the arterial line 104 to an arterial pressure sensor 106. The blood then flows through a segment of blood line abutting a pump 108, which may be a peristaltic pump. The pump 108 forces the blood through the extracorporeal blood circuit 100 toward a dialyzer 110. The blood then flows through the dialyzer 110 where waste and excess water in the blood may be removed. The detoxified blood then flows through a venous pressure sensor 112 and into an air-release chamber 114 which functions to remove gas, or air, from the blood before it is returned to patient 102 through the venous line 116.

Figure 2B:
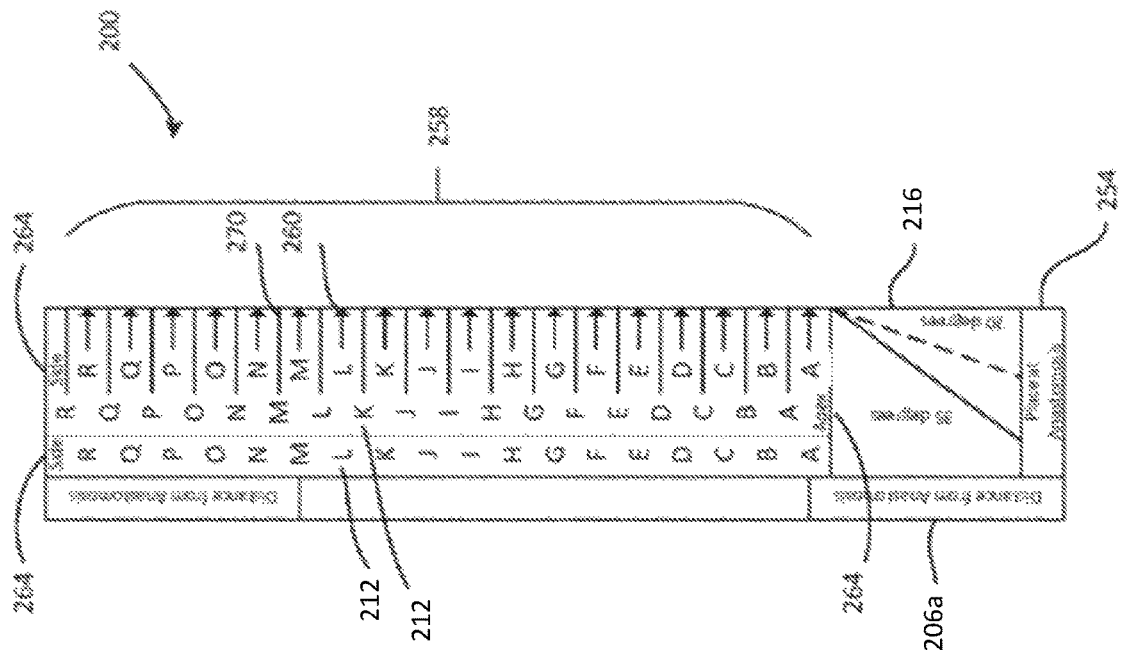
FIGS. 2A and 2B are views of first and second sides, respectively, of a cannulation site selection apparatus with markings for use with an arteriovenous fistula, which may be used in creating vascular access to the patient for hemodialysis treatment.
Figure 2A:
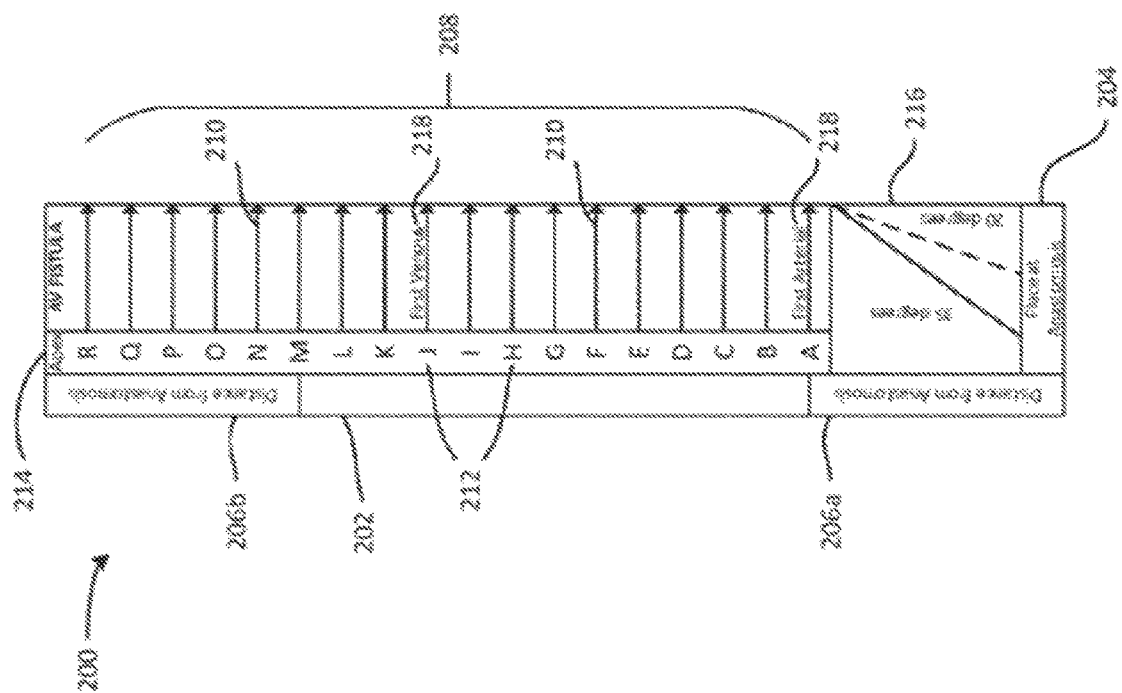

Certain cannulation site selection apparatuses described herein can be used to assist users with properly inserting arterial and venous needles into arterial and venous needle sites to carry out hemodialysis treatments of the type described above. FIGS. 2A and 2B show two sides of a cannulation site selection apparatus 200 to be used for a patient with an arteriovenous fistula. FIG. 2A shows markings for planning and selecting cannulation sites if the user would like to use the apex of the vessel wall for cannulation. FIG. 2B shows markings for planning and selecting cannulation sites if sides of the vessel are desired to be used for cannulation in addition to the apex. The cannulation site selection apparatus 200 includes a flexible member 202 with a first marking 204 located at one end of the cannulation site selection apparatus. The first marking 204 indicates that the user should place the first marking 204 at the patient's anastomosis. An anastomosis is a connection made surgically between adjacent blood vessels, or other channels of the body. A distance marking 206a is used to measure a distance from a patient's anastomosis to a first site for arterial cannulation. In the shown embodiment, the distance between the anastomosis and the first site for arterial cannulation is 1.5 inches. A second distance marking 206b is located on the second end of the cannulation site selection apparatus to allow a user to measure a distance from an anastomosis with either end of the apparatus.

The cannulation site selection apparatus 200 also includes an array 208 of cannulation site selection markings 210. For an apparatus to be used with an arteriovenous fistula, the cannulation site selection markings 210 are typically spaced 0.25 inches apart. The cannulation site selection markings 210 correspond with cannulation site labels 212. The cannulation site labels 212, in this embodiment, are the letters A through R. The cannulation site labels are marked with an access position label 214 to indicate where along the vessel cannulation should occur. In this embodiment, the access position label 214 indicates that cannulation should occur at the apex of the vessel. The cannulation site selection apparatus 200 also includes first treatment labels 218. First treatment labels 218 indicate recommended cannulation sites for a first treatment. In this embodiment, the first treatment labels 218 indicate two sites—one arterial and one venous—that are spaced to allow the maximum number of available cannulation sites to be used in subsequent treatments. Additionally, the cannulation site selection apparatus 200 includes an angle guide marking 216 which a user may reference in inserting a needle at an angle appropriate for cannulating a fistula. In this example, an appropriate angle is between 20 and 35 degrees. This embodiment of the cannulation site selection apparatus 200 is 6.0 inches long and 1.25 inches wide.

As shown in FIG. 2B, the opposite side of the cannulation site selection apparatus 200 includes a secondary set of cannulation site selection markings 270 indicating additional available cannulation sites on a patient's arteriovenous fistula. The secondary cannulation site selection markings 270 are included in the array 258. Here, the secondary cannulation site selection markings 270 are labeled by access position labels 264 for use in marking cannulation sites along the sides of a vessel. The secondary cannulation site selection markings 270 can also be used to indicate cannulation sites for a second pass over the vessel, increasing the total number of available cannulation sites before a site is repeated and therefore extending the length of the cannulation site rotation plan. For an arteriovenous fistula, the cannulation site selection markings 260 are typically spaced 0.25 inches apart. The secondary cannulation site selection markings 270 are offset from the cannulation site selection markings 260 by 0.125 inches (or ⅛ inch) and are also typically spaced 0.25 inches apart.

The markings on the flexible member are substantially permanent so as not to be smudged or wiped away upon sterilization of the apparatus between uses. Sterilization may be performed by submerging the apparatus in a 1% bleach solution for twenty minutes. As a result, the apparatus is reusable and easy to clean.

The markings of the apparatus may also be of different colors so as to make the markings easier to read or distinguish from one another. For example, the cannulation site selection markings 260 and the secondary cannulation site selection markings 270 may be in contrasting colors, such as red and blue.

The cannulation site selection markings on the apparatus may be of differing shapes. These differing shapes are shown in FIG. 2B as the cannulation site selection markings 260 are arrow shapes and the secondary cannulation site selection markings 270 are lines. This can help the user to distinguish the cannulation site selection markings 210 from the secondary cannulation site selection markings 270.

Figure 3A:
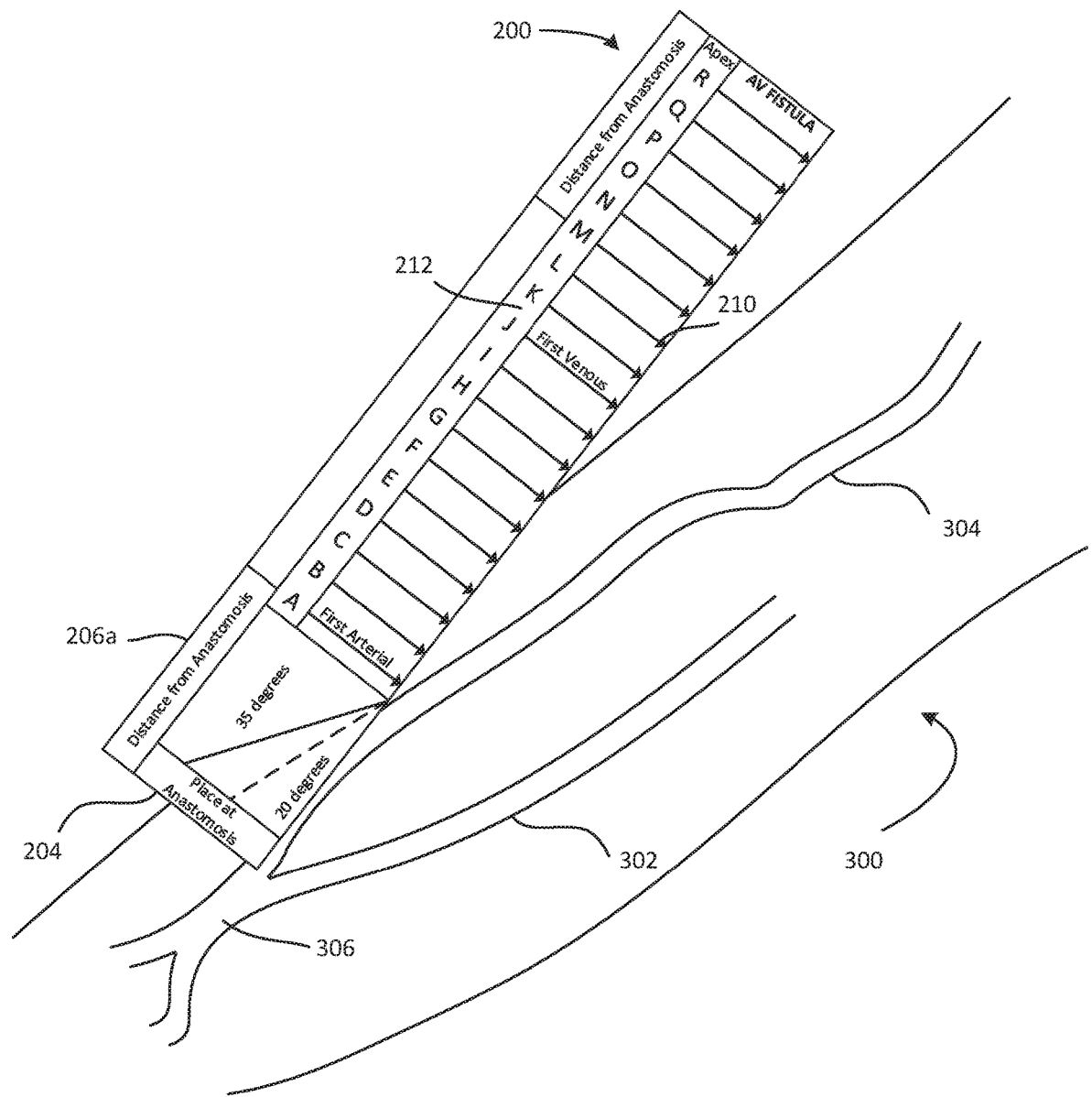
FIGS. 3A-3E depict a method of using the cannulation site selection apparatus of FIGS. 2A and 2B for creating vascular access to a patient with an arteriovenous fistula.

FIGS. 3A through 3E show a method of using a cannulation site selection apparatus 200 with an arteriovenous fistula. As shown in FIG. 3A, a user places a first marking 204 on the patient's arm 300 (or another bodily area where vascular access is obtained) at the arteriovenous anastomosis 306. An anastomosis is a connection made surgically between adjacent blood vessels, or other channels of the body. Here, anastomosis 306 connects an artery 302 with a vein 304.

Figure 3B:
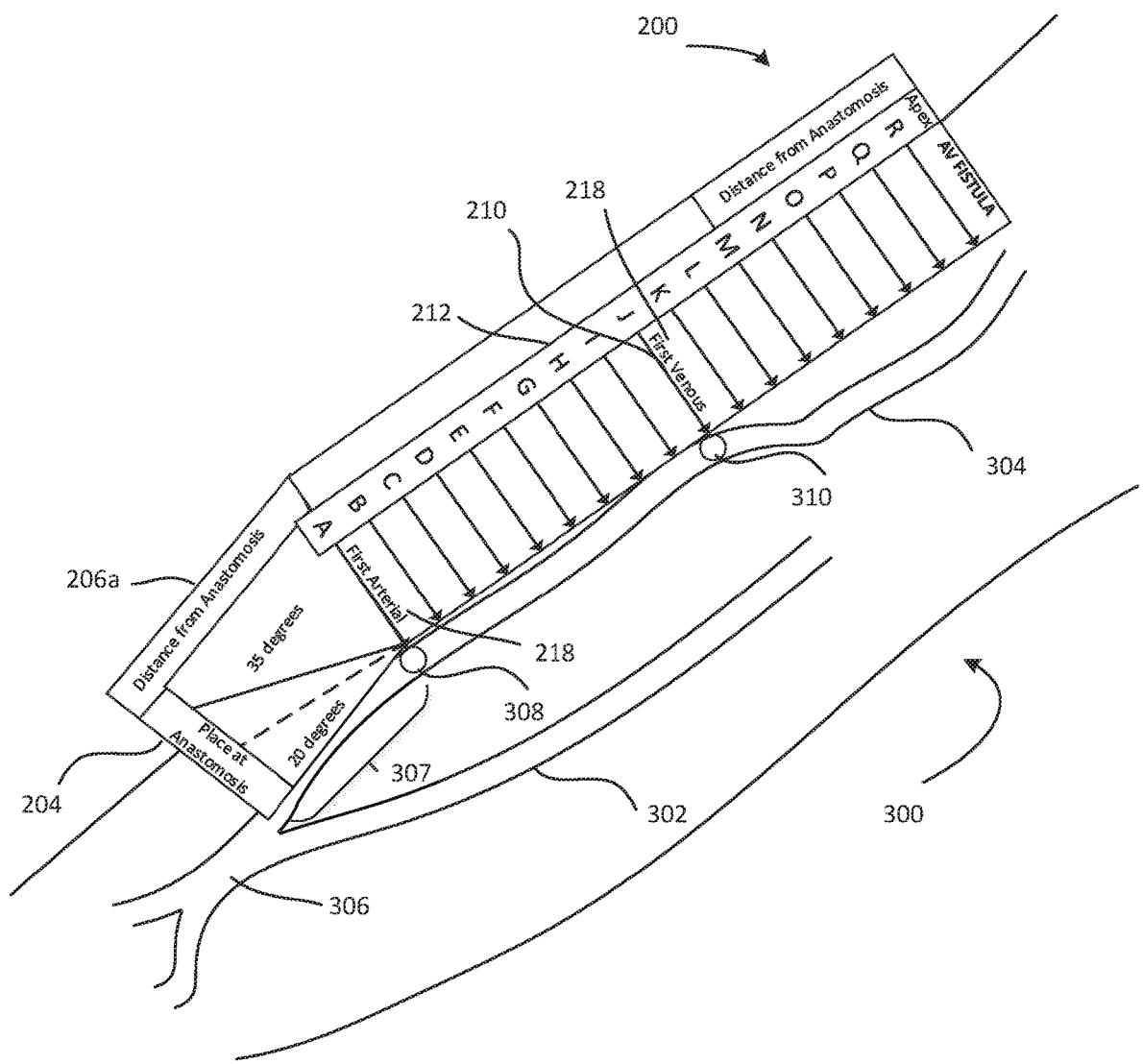

As shown in FIG. 3B, the user orients the apparatus 200 along a vessel 304 that will be used to create the vascular access. In orienting the apparatus 200 along the vessel 304, the user places the first marking 204 at the anastomosis 306. The flexibility of the apparatus 200 allows the user to contour the apparatus 200 along the vessel 304. As the apparatus 200 is contoured along the vessel 304, distance marking 206a, which measures a distance between the anastomosis 306 and a first cannulation site selection marking 210 in the array 208, creates a visual "no stick zone" 307 along the vessel 304, indicating to the user that no needles should be inserted in that area.

To set up a cannulation site rotation plan, a user determines the number of available cannulation sites along the vessel 304 based on the number of cannulation site selection markings 210 corresponding to viable locations for cannulation along the vessel. The viability of a vessel location for cannulation depends on many factors, including vessel integrity, shape, and size. Based on the number of available cannulation sites, a user calculates a number of treatments that can be completed before repeating a cannulation site. The patient shown in FIGS. 3A-3E has 18 available cannulation sites, each one corresponding to a cannulation site selection marking 210 on the apparatus 200. Each of these cannulation site selection markings 210 corresponds with a cannulation site label 212, here the letters A-R. In this embodiment, the cannulation sites associated with labels A-I will be cannulated for arterial access and the cannulation sites associated with labels J-R will be cannulated for venous access.

With these 18 available cannulation sites, given that two sites will be needed for each hemodialysis treatment, and that the patient requires three hemodialysis treatments per week, a three-week rotation plan for cannulation sites can be created. A sample three-week site selection plan based on 18 available cannulation sites and three hemodialysis treatments per week is shown below:

| Site Rotation Plan Example | | |
| --- | --- | --- |
| | Arterial Site | Venous Site |
| Week 1 | | |
| Mon | A | J |
| Wed | B | K |
| Fri | C | L |
| Week 2 | | |
| Mon | D | M |
| Wed | E | N |
| Fri | F | O |
| Week 3 | | |
| Mon | G | P |
| Wed | H | Q |
| Fri | I | R |

Starting with site A for the arterial access and site J for the venous access at the first treatment, each treatment may use a new pair of sites until treatment at the site I for the arterial access and R for the venous access is completed. Then, at the next treatment, the user would return to re-cannulate sites A and J.

Additionally, as shown on the second side of cannulation site selection apparatus 200, depicted in FIG. 2B, there are secondary markings 220 included in the array 208, which may identify additional cannulation sites along a vessel to be checked by the user for viability. If the secondary markings 220 correspond to additional cannulation sites that are viable for cannulation, the site rotation plan may be extended. For example, the site rotation plan can be extended to at least six weeks if a user determines all of the cannulation sites corresponding to the secondary markings 220 are viable while using the second side of the cannulation site selection apparatus 200 (shown in FIG. 2B). Additional lengthening of the site rotation plan can be achieved by using the sides of the vessel for cannulation. The second side of the cannulation site selection apparatus 200, shown in FIG. 2B, can extend a site rotation plan up to 18 weeks. In an 18-week plan, both sides of the vessel and the apex of the vessel would be cannulated at sites corresponding to each of the cannulation site selection markings and the secondary site selection markings.

For a first treatment, as is shown in FIG. 3B, the user may use first treatment labels 218, which show a first available arterial needle site and a first available venous needle site that are spaced to safely separate the arterial and venous needles during treatment, to determine a first arterial cannulation site 308 and a first venous cannulation site 310. If one of these sites is not viable based on the condition of the vessel, the user may modify their choice of access site to correspond to another cannulation site selection marking 210 on the apparatus 200.

Figure 3C:
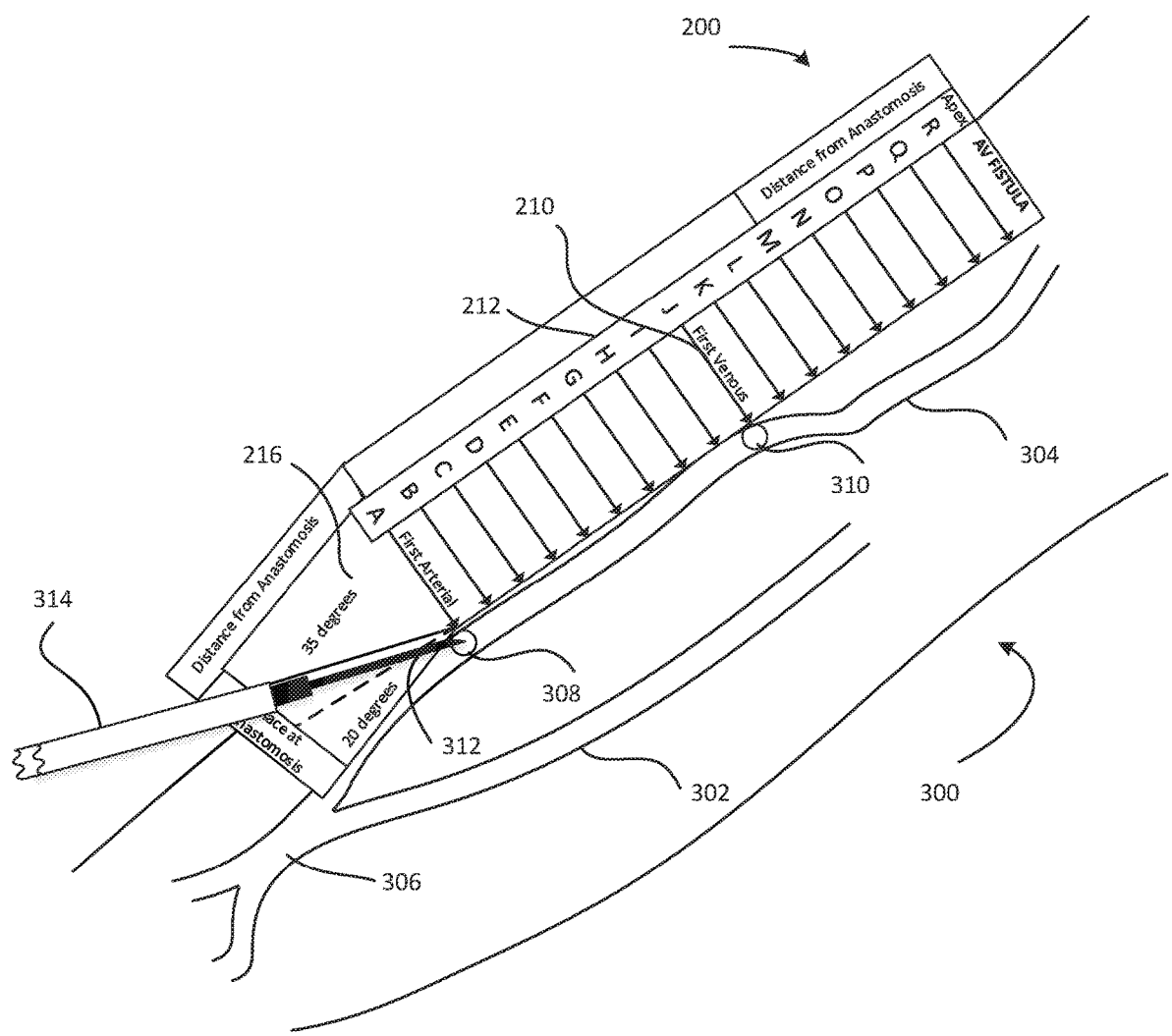

As shown in FIG. 3C, the user will then cannulate at each of the chosen cannulation sites 308, and 310. The user may reference the angle guide marking 216 to cannulate the vessel 304 with a needle 312 at a preferred angle. Here the preferred angle is between 20 and 35 degrees. Inserting the needle 312 into the vessel at site 308 provides arterial vascular access to the patient. During hemodialysis treatment, the patient's blood will flow from the vessel 304, through the needle 312, and into tubing 314. Tubing 314 is part of the arterial line 104. The blood will then proceed through the extracorporeal blood circuit and is returned through the needle (not shown) inserted into the vessel at site 310. When treatment is completed, the needles are removed, and the cannulated sites 308 and 310 may begin to heal. Because of the design of the cannulation site selection apparatus 200, sites 308 and 310 will typically not be re-cannulated until all other possible cannulation sites have been used. In this embodiment, sites 308 and 310 will have three weeks to heal before re-cannulation.

Figure 3D:
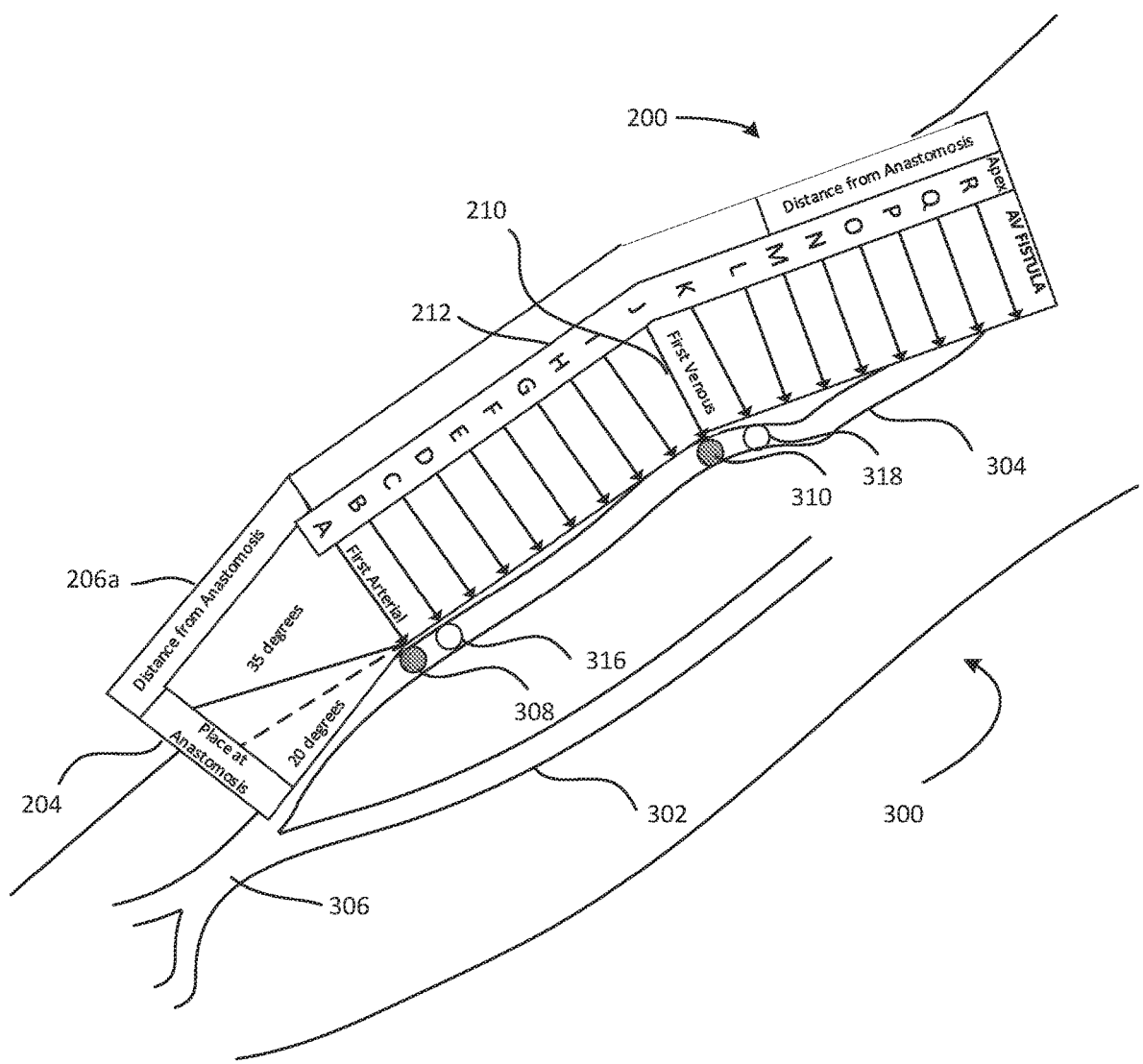

As shown in FIG. 3D, when the patient requires a subsequent treatment, the user will begin by placing the first marking 204 at the anastomosis 306 of the patient and orienting the array 208 of cannulation site selection markings 210 along the vessel 304. The user will then select a new set of cannulation sites to use for access. The user may select cannulation sites for a new treatment by referring to a cannulation site selection plan. In this embodiment, as cannulation sites 308 and 310, associated with site selection labels A and J, respectively, were used in the previous treatment, cannulation sites 316 and 318, associated with site selection labels B and K, respectively, are selected for use.

The user may also select new cannulation sites by measuring from a previously cannulated site. The user aligns the previously cannulated site with a cannulation site selection marking 210 on the apparatus 200, keeping in mind the distance from the anastomosis 306 indicated by distance marking 206a should be observed and sticking needles within that distance should be avoided. After aligning a cannulation site selection marking 210 with a previously used cannulation site, the user may re-assess the viability of the remaining available cannulation sites. The user would then choose a cannulation site at an adjacent cannulation site selection marking 210 assuming the site is viable. For example, a user may align the cannulation site selection marking 210 associated with cannulation site label A with the previously used cannulation site. The user would check that the anastomosis is at least as far away as the distance marker 206a suggests. Then, as long as the cannulation site on the vessel identified by cannulation site selection marking associated with cannulation site label B is viable, the user would select site B for cannulation.

Figure 3E:
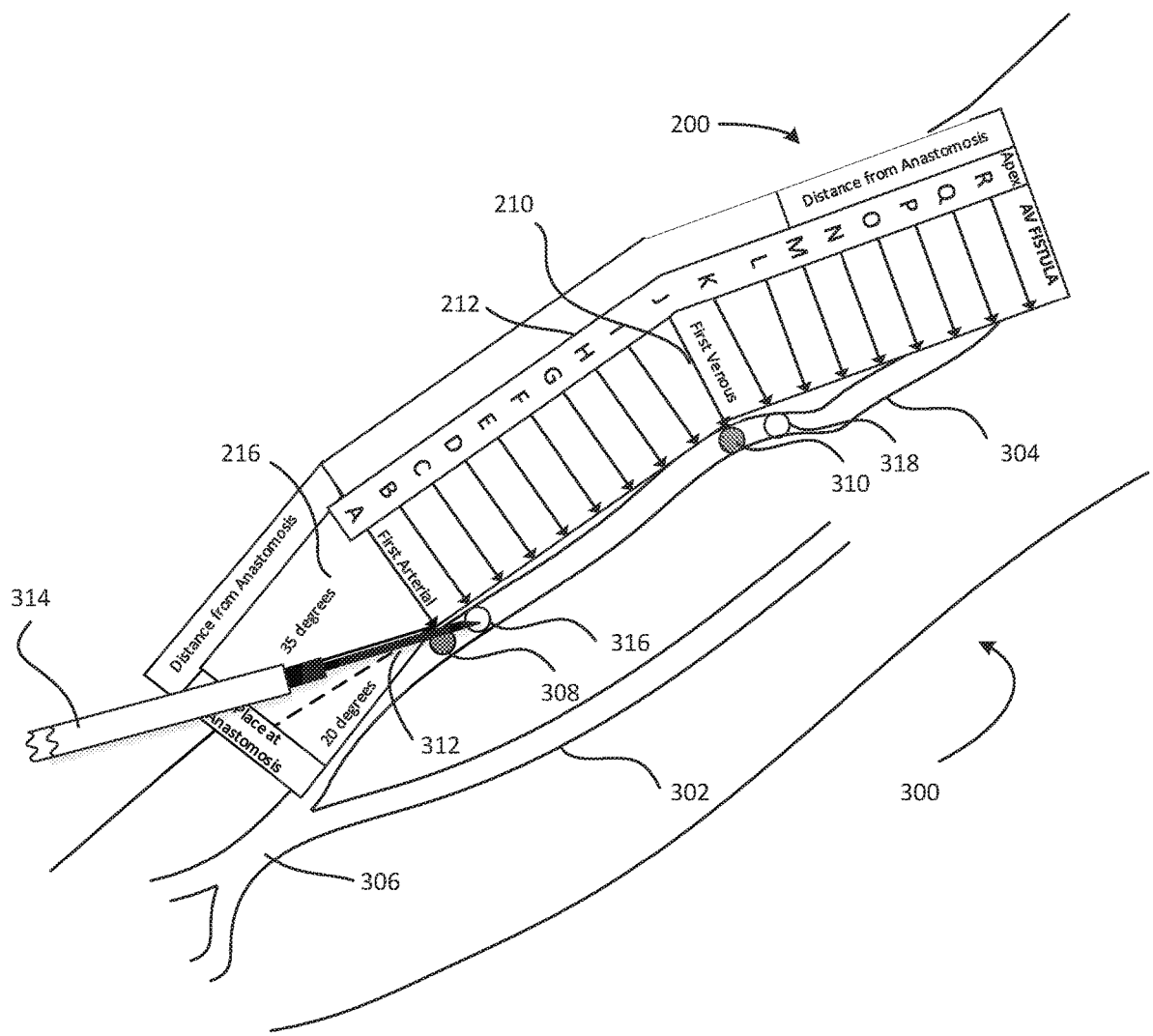

As shown in FIG. 3E, the user cannulates the newly selected site 316 with a needle 312 to provide arterial vascular access to vessel 304 for hemodialysis treatment. The user also cannulates site 318 with a second needle to provide venous vascular access to vessel 304 for hemodialysis treatment. The blood will be removed from the patient through needle 312 inserted at site 316 and returned through the second needle inserted at site 318. When treatment is completed, the needles are removed, and the cannulated sites 316 and 318 may begin to heal. Because of the design of the cannulation site selection apparatus 200, sites 316 and 318 will typically not be re-cannulated until all other possible cannulation sites have been used. In this embodiment, sites 316 and 318 will have three weeks to heal before re-cannulation.

Figure 4A:
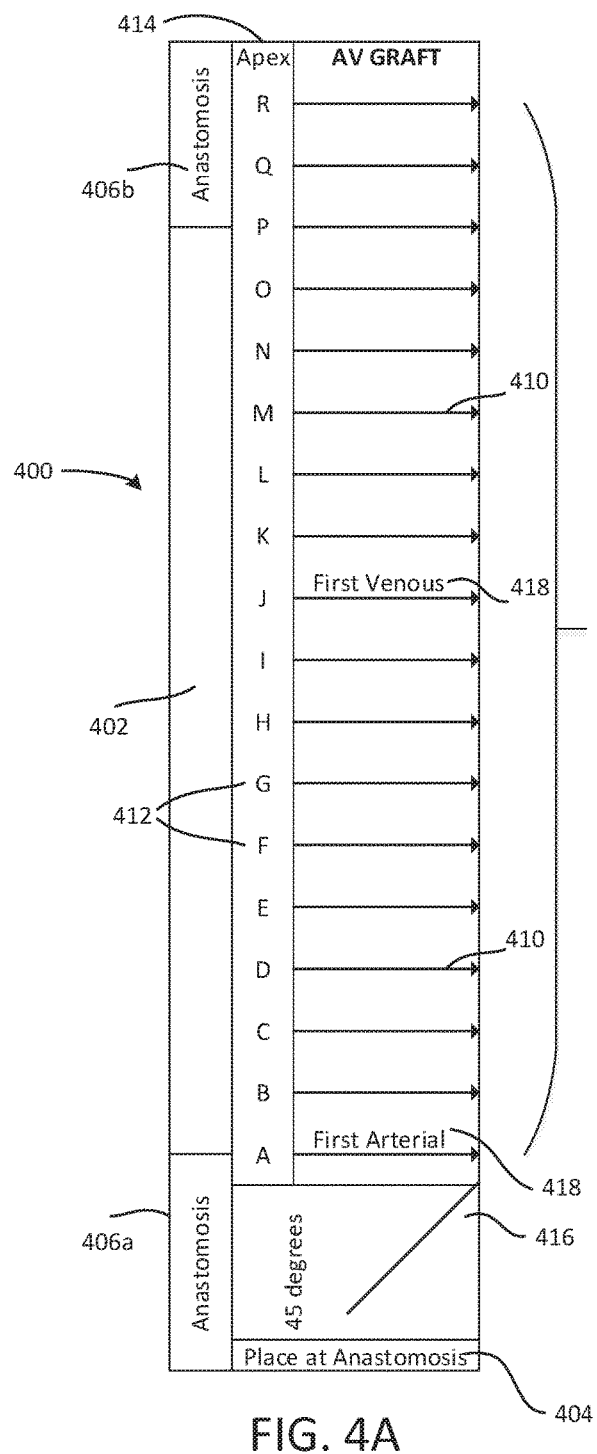
FIGS. 4A and 4B are views of first and second sides, respectively, of another cannulation site selection apparatus with markings for use with an arteriovenous graft, which may be used in creating vascular access to the patient for hemodialysis treatment.
Figure 4B:
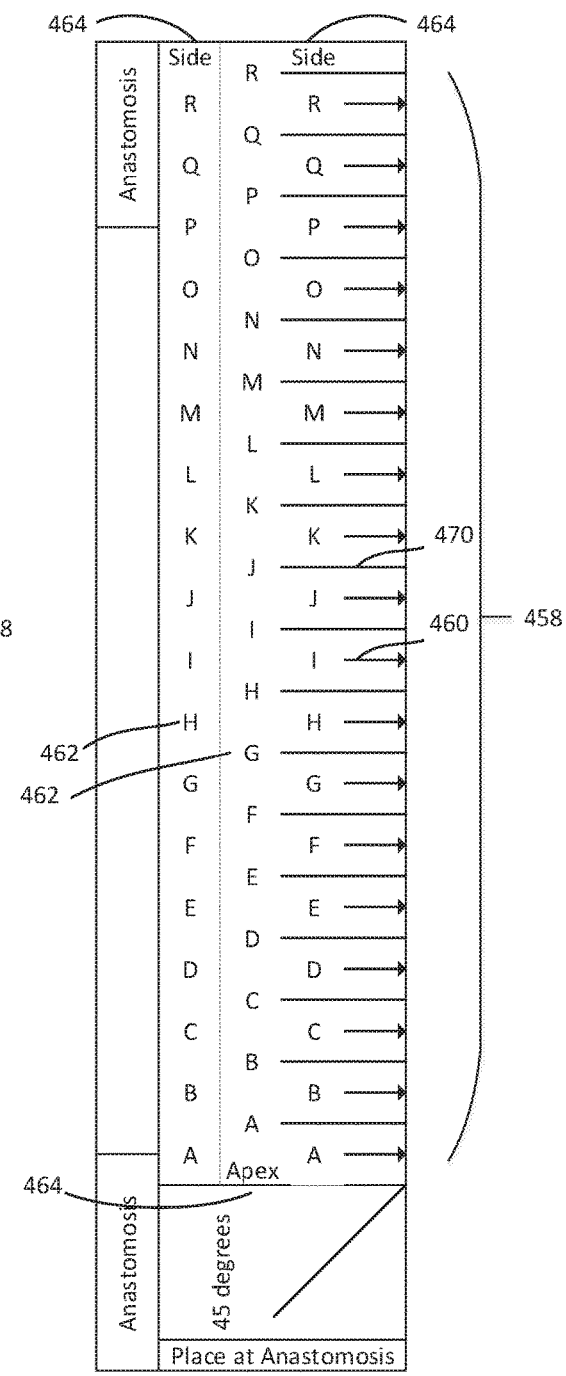

FIGS. 4A and 4B are views of first and second sides, respectively, of an embodiment of a cannulation site selection apparatus 400 with markings for use with an AV graft. FIG. 4A shows markings for planning and selecting cannulation sites if the user would like to use the apex of the vessel wall for cannulation. FIG. 4B shows markings for planning and selecting cannulation sites if sides of the vessel are available for cannulation. The cannulation site selection apparatus 400 includes a flexible member 402 with a first marking 404 located at one end of the cannulation site selection apparatus. The first marking 404 allows a user to orient the cannulation site selection apparatus appropriately on a patient's arteriovenous graft. A distance marking 406a is used to measure a distance from an anastomosis to a first site for arterial cannulation. In the shown embodiment, the distance between the anastomosis and the first site for arterial cannulation is 3.0 cm. A second distance marking 406b is located on the second end of the cannulation site selection apparatus to allow a user to measure a distance from an anastomosis with either end of the apparatus. As many arteriovenous grafts form a looped shape, the user may use both distance markings 406a and 406b to ensure that cannulation sites are not too close to either anastomosis of the arteriovenous graft.

The cannulation site selection apparatus 400 also includes an array 408 of cannulation site selection markings 410. For an arteriovenous graft, the cannulation site selection markings 410 are typically spaced 0.5 cm apart. These markings may correspond with cannulation site labels 412, which, in this embodiment, are the letters A through R. The cannulation site labels may be marked with an access position label 414 to indicate where along the vessel cannulation should occur. In this embodiment, the access position label 414 indicates that cannulation should occur at the apex of the vessel. The cannulation site selection apparatus 400 may also include first treatment labels 418 indicating recommended cannulation sites for a first treatment. The first treatment labels 418 indicate two sites, one arterial and one venous, that are properly spaced from the anastomosis and allow the maximum number of available cannulation sites to be used in subsequent treatments. Additionally, the cannulation site selection apparatus 400 may also include a cannulation angle guide marking 416 which a user may use as a reference in inserting a needle at an angle appropriate for cannulation of a fistula. In this embodiment, for use with an arteriovenous graft, an appropriate angle is approximately 45 degrees.

As shown in FIG. 4B, the cannulation site selection apparatus 400 also includes a secondary set of cannulation site selection markings 470 indicating additional available cannulation sites on a patient's arteriovenous fistula. The secondary cannulation site selection markings 470 are included in the array 458. Here, the secondary cannulation site selection markings 470 are labeled by access position labels 464 for use as cannulation sites along the sides of a vessel. The secondary cannulation site selection markings 470 can also be used to indicate cannulation sites for a second pass over the vessel, increasing the total number of available cannulation sites before a site is repeated and therefore extending the length of the cannulation site rotation plan. For an arteriovenous graft, the cannulation site selection markings 460 are typically spaced 0.5 cm apart. The secondary cannulation site selection markings 470 are offset from the cannulation site selection markings 460 by 0.25 cm and are also typically spaced 0.5 cm apart The cannulation site selection apparatus 400 shown in FIGS. 4A and 4B is used in a method similar to the method of use shown for cannulation site selection apparatus 200 as discussed in view of FIGS. 3A-3E. The user will contour the apparatus 400 along the arteriovenous graft and select sites for cannulation using the cannulation sites selection markings 410 (or 460 and/or 470). The user may set up a cannulation site rotation plan based on the number of viable treatment sites corresponding to cannulation site selection markings 410 (or 460, and/or 470) on the apparatus 400. As many arteriovenous grafts form a looped shape, the user may use both distance markings 406a and 406b to ensure that cannulation sites are not too close to either anastomosis of an arteriovenous graft.

FIGS. 5A and 5B are views of first and second sides, respectively, of a cannulation site selection apparatus 500 with markings for use with an arteriovenous graft on the first side and with markings for use with an arteriovenous fistula on the second side. In this embodiment, the arteriovenous fistula apparatus markings take up a smaller area than the arteriovenous graft apparatus markings because of the differing vessel geometries for each vascular access type. The apparatus also includes a key 504 which includes a recommended cannulation site rotation plan.

Figure 6:
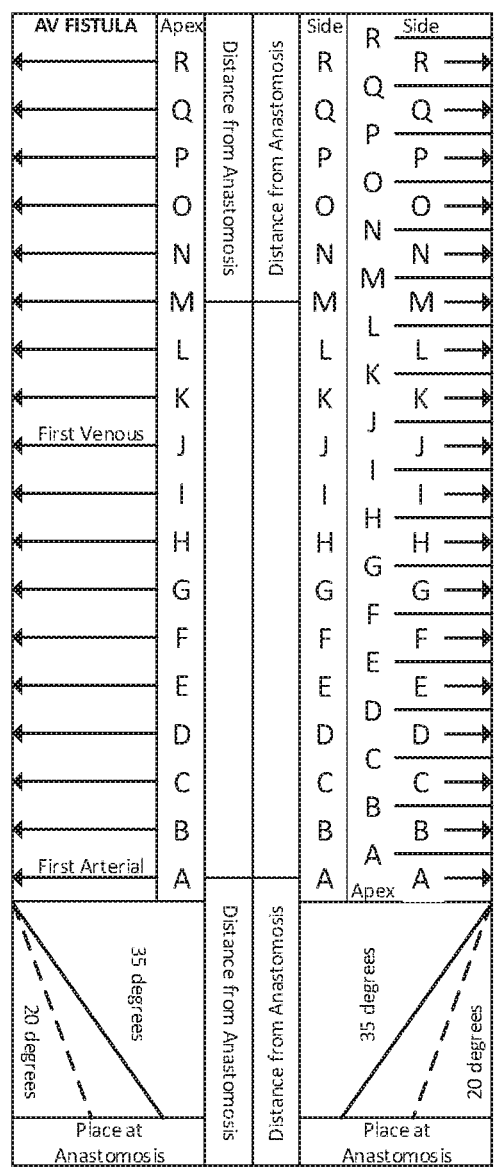
FIG. 6 depicts a double-edged embodiment of a cannulation site selection apparatus with markings for use with an arteriovenous fistula.
Figure 7:
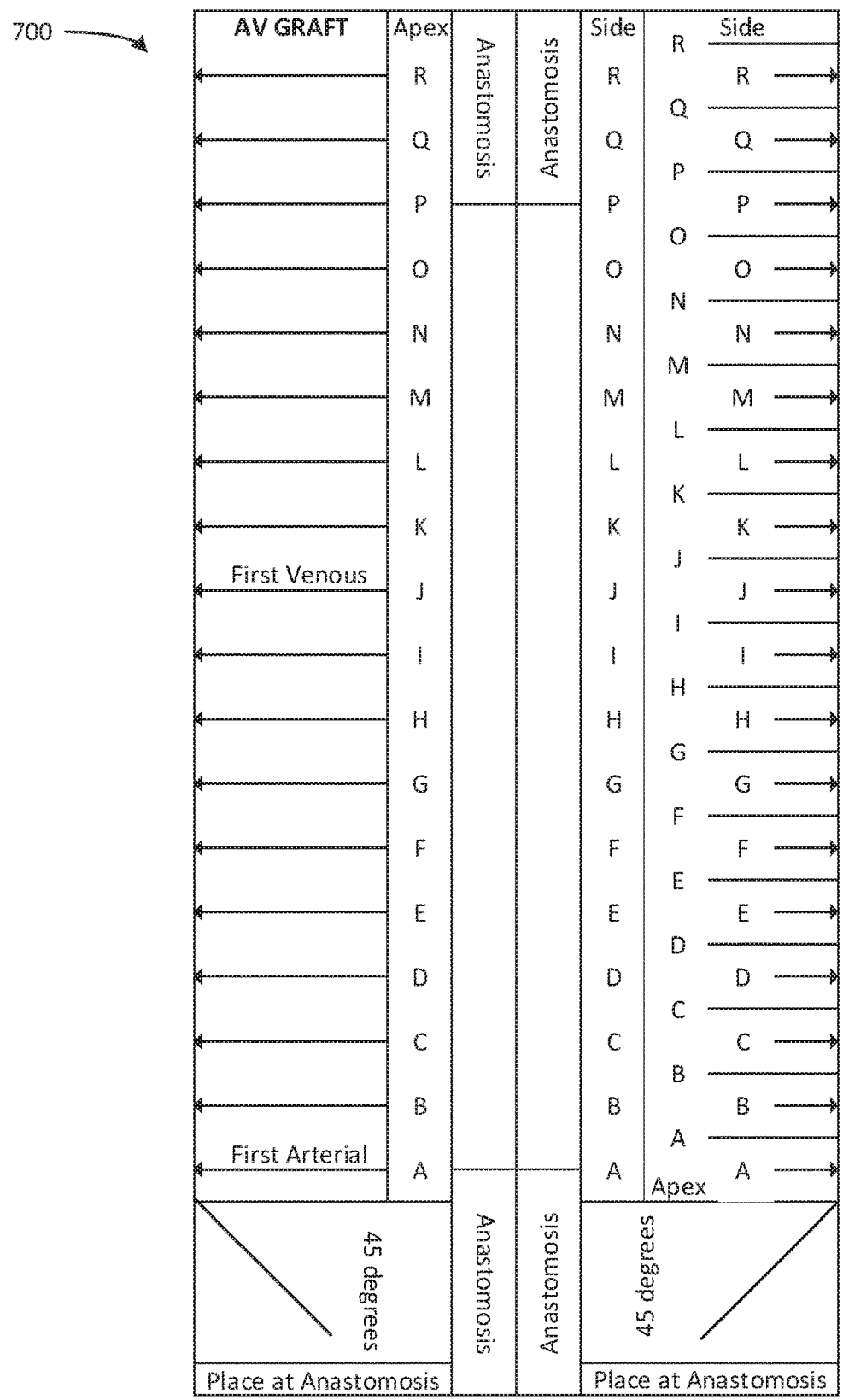
FIG. 7 depicts another double-edged embodiment of a cannulation site selection apparatus with markings for use with an arteriovenous graft.

FIGS. 6 and 7 depict double-edged embodiments of a cannulation site selection apparatuses 600 and 700 with markings for use with an arteriovenous fistula and for use with an arteriovenous graft, respectively. In FIGS. 6 and 7, the left side of each of the double-edged apparatuses 600 and 700 contain markings matching the first sides of apparatuses 200 and 400, respectively, as shown in FIGS. 2A and 4A. The right side of each of the double-edged apparatuses 600 and 700 contain markings matching the second sides of apparatuses 200 and 400, respectively, as shown in FIGS. 2B and 4B. In this embodiment, a user would be able to decide which array of cannulation site selection markings to use on a patient without flipping the apparatus over. This arrangement would also allow for a key, usage instructions, or other information to be printed on the opposite side of the apparatus. Alternatively, this configuration of markings could be disposed on a flexible member that is translucent, as the arrays both including and lacking secondary markings would be available on the same side of the apparatus.

Figure 8A:
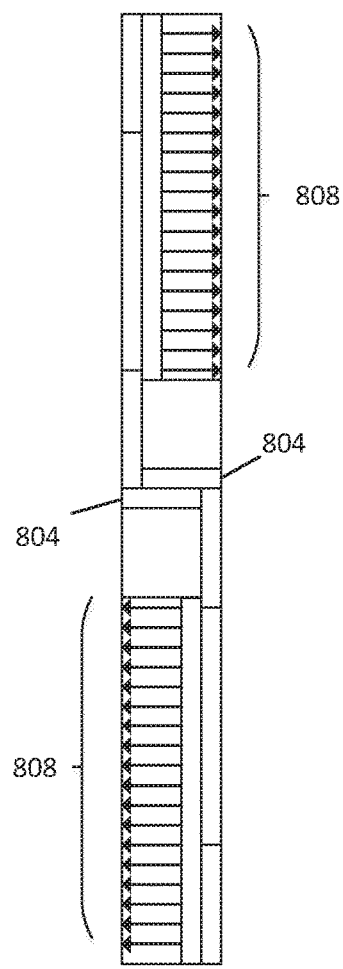
FIGS. 8A-8D depict embodiments of cannulation site selection apparatuses with varying orientations of markings.
Figure 8B:
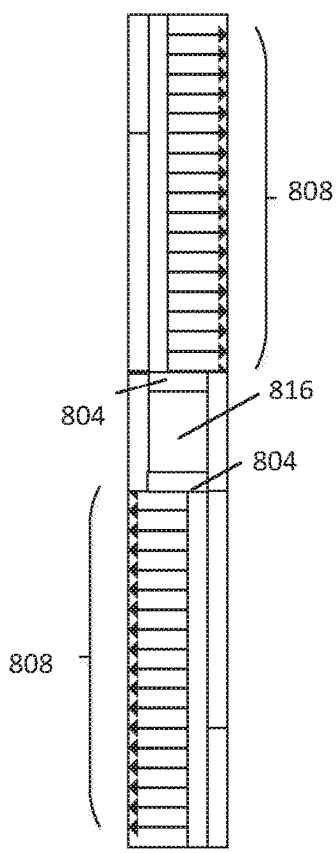
Figure 8C:
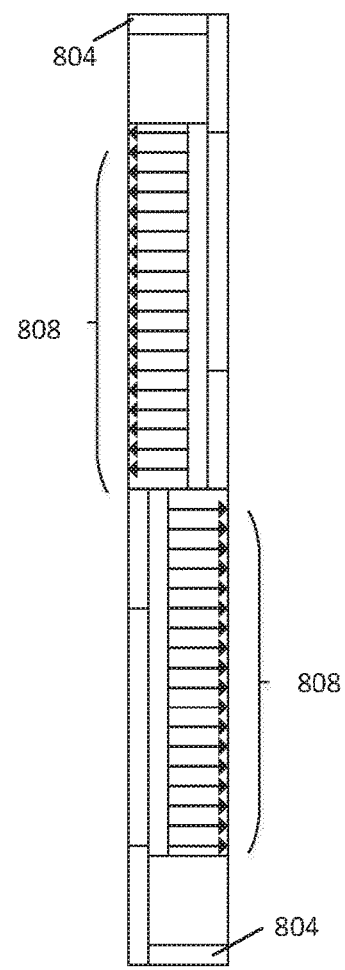
Figure 8D:
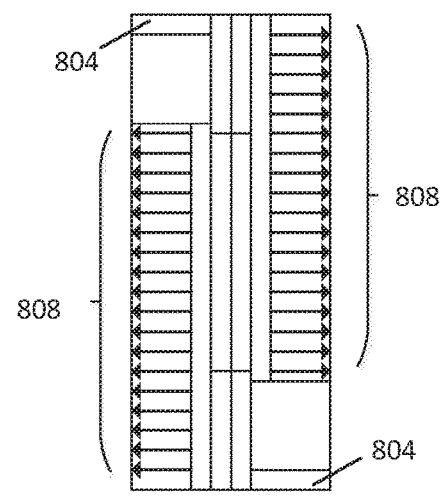

FIGS. 8A-8D depict embodiments of cannulation site selection apparatuses with varying orientations of markings. FIG. 8A shows an embodiment of a cannulation site selection apparatus where the first markings 804 are located toward the center of the apparatus and the arrays 808 of cannulation site selection markings point off opposite edges of the apparatus. FIG. 8B shows an embodiment of a cannulation site selection apparatus with two arrays 808 of cannulation site selection markings and one angle guide marking 816. The angle guide marking 816 in this embodiment may contain multiple angle markings such that the guide may be used in cannulating a vessel using either array of cannulation site selection markings. FIG. 8C shows an embodiment of a cannulation site selection apparatus where the first markings 804 are located at opposite ends of the apparatus, and the arrays 808 of cannulation site selection markings point off opposite edges of the apparatus. FIG. 8D shows an embodiment of a double-edged apparatus with the first markings 804 disposed on opposite ends of the apparatus and the arrays 808 of cannulation site selection markings pointing off opposite edges of the apparatus.

While the cannulation site selection apparatuses of the embodiments shown and discussed above are rectangular in shape, apparatuses of other shapes and dimensions could also be used. For example, a cannulation site selection apparatus may have a curved edge such that the apparatus could be rocked along a vessel for determining available cannulation sites or measuring from one site to the next.

While the cannulation site selection apparatuses of the embodiments shown and discussed above include cannulation site selection markings disposed on a flexible member, the flexible member may include other features to aid the user in selecting cannulation sites. For example, in addition to or alternative to cannulation site selection markings, a cannulation site selection apparatus may have notches along an edge of the flexible member or holes in the flexible member. Notches along an edge of a cannulation site selection apparatus could aid the user in visualizing cannulation sites as the notches may help to frame individual sites.

Holes in the body of the flexible member could allow cannulation through the flexible member. The user could lay the apparatus flat on the vessel, determine cannulation sites, and cannulate through the hole at that cannulation site. An apparatus with holes could further indicate that the user should avoid cannulating the vessel at undesirable locations, such as, for example, in a "no stick zone" near an anastomosis, because there would not be a hole to cannulate through at those locations. The holes could additionally be slit such that the apparatus would be removable from the patient after vascular access is achieved through cannulation. After cannulating the vessel through a hole, the user could bend the flexible member at the slit and slide the apparatus off of the needle or tubing.

While the cannulation site selection apparatuses of the embodiments shown and discussed above are discussed mainly in the context of a two-needle vascular access scheme, the cannulation site selection apparatuses can also be used for single needle dialysis, or for other methods of creating vascular access. In single needle dialysis, one needle is inserted into a vessel. The dialysis machine cycles between removing blood from the patient and delivering blood to the patient through the single needle. Rotating cannulation sites for single needle dialysis allows for increased tissue healing and reduces the likelihood of vascular access failures.

While the cannulation site selection apparatuses of the embodiments shown and discussed above are discussed mainly for use with traditional cannulation methods, the cannulation site selection apparatus can also be useful in implementing the buttonhole cannulation method for patients with an arteriovenous fistula. In buttonhole cannulation, a needle is repeatedly inserted at one site, at the same angle, to form a channel, or tunnel track, of scar tissue. After the tunnel is formed, duller needles may be inserted along the tunnel track to create vascular access for hemodialysis treatment. The buttonhole cannulation method may be less painful for patients than traditional methods as duller needles are used to avoid cutting the scar tissue channel. The cannulation site selection apparatus may be useful for buttonhole cannulation because the angle guide marking allows a user to ensure that the same angle is used for inserting a needle at each treatment. Using the same insertion angle for each treatment is especially important when establishing the scar tissue channel. Additionally, for subsequent treatments, using the angle guide marking can improve accuracy in following the scar tissue channel.

While the cannulation site selection apparatuses of the embodiments shown and discussed above are discussed mainly for use in cannulating a patient for hemodialysis treatments, the cannulation site selection apparatuses may be used in cannulating patients for hemofiltration, hemodiafiltration, ultrafiltration, or other medical treatments where cannulation or insertion of an instrument into the body at a particular position or angle is necessary.

While the markings of the cannulation site selection apparatuses of the embodiments shown and discussed above are discussed in the context of being resistant to wear during a twenty-minute soak in 1% bleach solution for sterilization, the markings may be designed to withstand degradation during other sterilization procedures. These other sterilization procedures may include sterilization by ultraviolet light, a higher or lower concentration of bleach (for a longer or shorter soaking time), or hydrogen peroxide.

While the cannulation site selection apparatuses of the embodiments shown and discussed are discussed in the context of cannulating a patient's arm, the cannulation site selection apparatuses may be used with other vascular access positions on a patient. These other positions may include, the leg, the neck, the chest, or the groin.

The invention claimed is:

1. A cannulation site selection apparatus comprising:
   a flexible member;
   a first marking on the flexible member, the first marking identifying a portion of the cannulation site selection apparatus to be placed at a patient's blood vessel anastomosis; and
   an array of cannulation site selection markings on the flexible member, wherein the array of cannulation site selection markings includes: (i) arterial cannulation site selection markings and (ii) venous cannulation site selection markings,
   wherein the arterial cannulation site selection markings are positioned between the first marking and the venous cannulation site selection markings,
   wherein a first available arterial cannulation site selection marking of the arterial cannulation site selection markings is positioned at a first set distance from the first marking to define an area of the patient therebetween in which no cannulation needles should be inserted, and
   wherein the cannulation site selection markings are spaced at a second set distance from one another that is less than the first set distance.

2. The cannulation site selection apparatus of claim 1 wherein the second set distance at which the cannulation site selection markings are spaced is appropriate for use with an arteriovenous fistula.

3. The cannulation site selection apparatus of claim 1 wherein the second set distance at which the cannulation site selection markings are spaced is appropriate for use with an arteriovenous graft.

4. The cannulation site selection apparatus of claim 1 wherein the array of cannulation site selection markings comprises eighteen different cannulation site selection markings.

5. The cannulation site selection apparatus of claim 1 wherein the array of cannulation site selection markings comprises thirty-six different cannulation site selection markings.

6. The cannulation site selection apparatus of claim 1 further comprising an angle guide marking located between the first marking and the first available arterial cannulation site selection marking and arranged to represent an angle at which the user can insert a cannulation needle into a patient.

7. The cannulation site selection apparatus of claim 6 wherein the angle guide marking is configured to guide a user in cannulating an arteriovenous fistula.

8. The cannulation site selection apparatus of claim 6 wherein the angle guide marking is configured to guide a user in cannulating an arteriovenous graft.

9. The cannulation site selection apparatus of claim 1 wherein the array of cannulation site selection markings includes cannulation site selection markings for cannulating an apex and sides of a vessel wall.

10. The cannulation site selection apparatus of claim 1 wherein the flexible member includes cannulation site selection markings on first and second sides of the flexible member.

11. The cannulation site selection apparatus of claim 1 wherein the venous cannulation site selection markings includes a first available venous cannulation site.

12. The cannulation site selection apparatus of claim 1 wherein the flexible member is translucent.

13. The cannulation site selection apparatus of claim 1 wherein the flexible member defines notches along an edge of the flexible member and the notches are spaced at set distances from one another and correspond with the cannulation site selection markings.

14. The cannulation site selection apparatus of claim 1 wherein the flexible member defines holes spaced at set distances from one another and the holes correspond with the cannulation site selection markings.

15. The cannulation site selection apparatus of claim 1 further comprising a key on the flexible member, the key describing the array of cannulation site selection markings.

16. The cannulation site selection apparatus of claim 15 wherein the key includes a cannulation site rotation plan.

17. The cannulation site selection apparatus of claim 1 wherein the first marking and the cannulation site selection markings are substantially permanent so as to withstand repeated sterilization.

* * * * *